United States Patent
Ehinger et al.

(10) Patent No.: US 9,068,908 B2
(45) Date of Patent: Jun. 30, 2015

(54) SYSTEM AND METHOD FOR IMPROVING A WORKPIECE

(71) Applicant: Bell Helicopter Textron Inc., Fort Worth, TX (US)

(72) Inventors: Ryan T. Ehinger, Southlake, TX (US); Ron Woods, Weatherford, TX (US); David Bockmiller, Keller, TX (US)

(73) Assignee: Bell Helicopter Textron Inc., Fort Worth, TX (US)

(*) Notice: Subject to any disclaimer, the term of this patent is extended or adjusted under 35 U.S.C. 154(b) by 405 days.

(21) Appl. No.: 13/750,386

(22) Filed: Jan. 25, 2013

(65) Prior Publication Data

US 2014/0208861 A1 Jul. 31, 2014

(51) Int. Cl.

| | | |
|---|---|---|
| *B21C 37/30* | (2006.01) | |
| *B21D 53/38* | (2006.01) | |
| *C21D 7/06* | (2006.01) | |
| *G01N 3/02* | (2006.01) | |
| *C21D 7/04* | (2006.01) | |
| *C21D 10/00* | (2006.01) | |
| *F16H 55/17* | (2006.01) | |
| *G01M 13/02* | (2006.01) | |
| *C21D 7/02* | (2006.01) | |
| *F16H 57/00* | (2012.01) | |

(52) U.S. Cl.
CPC .. *G01N 3/02* (2013.01); *C21D 7/04* (2013.01); *C21D 7/02* (2013.01); *F16H 2057/0087* (2013.01); *C21D 10/005* (2013.01); *F16H 55/17* (2013.01); *G01M 13/021* (2013.01)

(58) Field of Classification Search
CPC .............. C21D 7/00; C21D 7/02; C21D 7/04; C21D 7/06; C21D 7/08; C21D 10/00; C21D 10/005; B21H 5/022
USPC .................... 29/90.6, 90.7, 893, 893.3; 72/53
See application file for complete search history.

(56) References Cited

U.S. PATENT DOCUMENTS

| | | | | |
|---|---|---|---|---|
| 5,841,033 | A | 11/1998 | Burris et al. | |
| 6,474,135 | B1* | 11/2002 | Clauer et al. | 73/12.01 |
| 6,923,877 | B1* | 8/2005 | Anderson | 148/525 |
| 7,159,425 | B2* | 1/2007 | Prevey et al. | 72/53 |
| 7,219,044 | B1* | 5/2007 | Prevey et al. | 703/7 |
| 7,513,121 | B2* | 4/2009 | Zurecki et al. | 62/64 |
| 7,762,113 | B2* | 7/2010 | Prevey, III | 72/53 |
| 7,832,070 | B2* | 11/2010 | Mordukhovich | 29/90.6 |
| 8,033,152 | B2* | 10/2011 | Prevey III | 72/53 |
| 8,511,130 | B2* | 8/2013 | Prevey, III | 72/377 |

(Continued)

OTHER PUBLICATIONS

European Search Report issued in EP Application No. 13190918.6 on Jun. 26, 2014, 4 pages.

(Continued)

*Primary Examiner* — Lisa Caputo
*Assistant Examiner* — Jonathan Dunlap
(74) *Attorney, Agent, or Firm* — Fish & Richardson P.C.

(57) ABSTRACT

A method of modifying a workpiece includes providing a workpiece, determining a load stress profile associated with a load condition, the load stress profile comprising a load stress greater than a material stress limit of the workpiece, determining a residual stress profile, the residual stress profile comprising a residual stress less than the material stress limit of the workpiece, and providing the workpiece with the residual stress profile, wherein a sum of the load stress and the residual stress is less than the material stress limit of the workpiece.

20 Claims, 2 Drawing Sheets

(56) References Cited

U.S. PATENT DOCUMENTS

| | | | |
|---|---|---|---|
| 2008/0032851 A1* | 2/2008 | Mordukhovich | 475/344 |
| 2008/0081208 A1* | 4/2008 | Prevey et al. | 428/610 |
| 2008/0127476 A1* | 6/2008 | Prevey | 29/402.04 |
| 2013/0074561 A1* | 3/2013 | Alberts et al. | 72/53 |
| 2013/0233040 A1* | 9/2013 | Butler et al. | 72/56 |

OTHER PUBLICATIONS

Paul Prevey et al. "Introduction of residual stresses to enhance fatigue performance in the initial design", Proceedings of Turbo Expo 2004, Vienna Austria Jun. 17, 2004; www.lambdatechs.com/documents/243.pdf, retrieved from internet on Jun. 18, 2014; XP007922734.

* cited by examiner

SYSTEM AND METHOD FOR IMPROVING A WORKPIECE

STATEMENT REGARDING FEDERALLY SPONSORED RESEARCH OR DEVELOPMENT

This invention was made with Government support under Agreement No. W911W6-10-2-0007 for Future Advanced Rotorcraft Drive System (FARDS). The Government has certain rights in the invention.

CROSS-REFERENCE TO RELATED APPLICATIONS

Not applicable.

REFERENCE TO A MICROFICHE APPENDIX

Not applicable.

BACKGROUND

Workpieces, such as, but not limited to, gears, may be exposed to loads that exceed material limits of the workpieces. In some cases, repeated or cyclic exposure to loads may lead to fatigue failure of a workpiece, especially when a workpiece is exposed to loads of vastly different directional components.

SUMMARY

In some embodiments of the disclosure, a method of modifying a workpiece is disclosed as comprising providing a workpiece, determining a load stress profile associated with a load condition, the load stress profile comprising a load stress greater than a material stress limit of the workpiece, determining a residual stress profile, the residual stress profile comprising a residual stress less than the material stress limit of the workpiece, and providing the workpiece with the residual stress profile, wherein a sum of the load stress and the residual stress is less than the material stress limit of the workpiece.

In other embodiments of the disclosure, an apparatus is disclosed as comprising processor configured to determine a tensile limit curve of the workpiece as a function of a dimension of the workpiece, determine a compressive limit curve of the workpiece as a function of the dimension of the workpiece, determine a tensile load stress profile associated with a tensile load condition, the tensile load stress profile comprising a tensile load stress curve as a function of the dimension of the workpiece, determine a compressive load stress profile associated with a compressive load condition, the compressive load stress profile comprising a compressive load stress curve as a function of the dimension of the workpiece, and determine a residual stress profile, the residual stress profile comprising a residual stress curve as a function of the dimension of the workpiece, wherein a summation of the residual stress curve and the tensile load stress curve is less than the tensile limit curve of the workpiece along the dimension, and wherein a summation of the residual stress curve and the compressive load stress curve is greater than the compressive limit curve along the dimension.

In yet other embodiments of the disclosure, an apparatus is disclosed as comprising a processor and a memory coupled to the processor, wherein the memory comprises instructions that cause the processor to determine a first contact stress associated with a mesh point of a tooth of a gear, determine a first bending stress associated with a root of the tooth, determine a first residual stress to the gear as a function of the first contact stress, and provide a second residual stress as a function of the first bending stress.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

In some cases, it may be desirable to improve a workpiece, such as, but not limited to, a load bearing component, by making the workpiece more resistant to failure as a result of deformation, internal restructuring, and/or fatigue. In some embodiments of the disclosure, systems and methods are disclosed that comprise determining a stress or stress profile that a workpiece may experience when exposed to a load or load profile and thereafter providing the workpiece with a residual stress or residual stress profile as a function of the stress or the stress profile so that the workpiece service life and/or strength may be improved.

Figure 1:
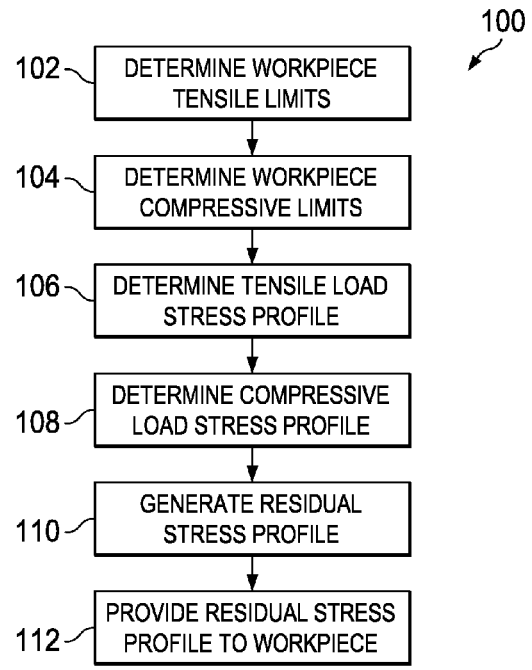
FIG. 1 is a flowchart of a method of improving a workpiece according to an embodiment of the disclosure.
Figure 2:
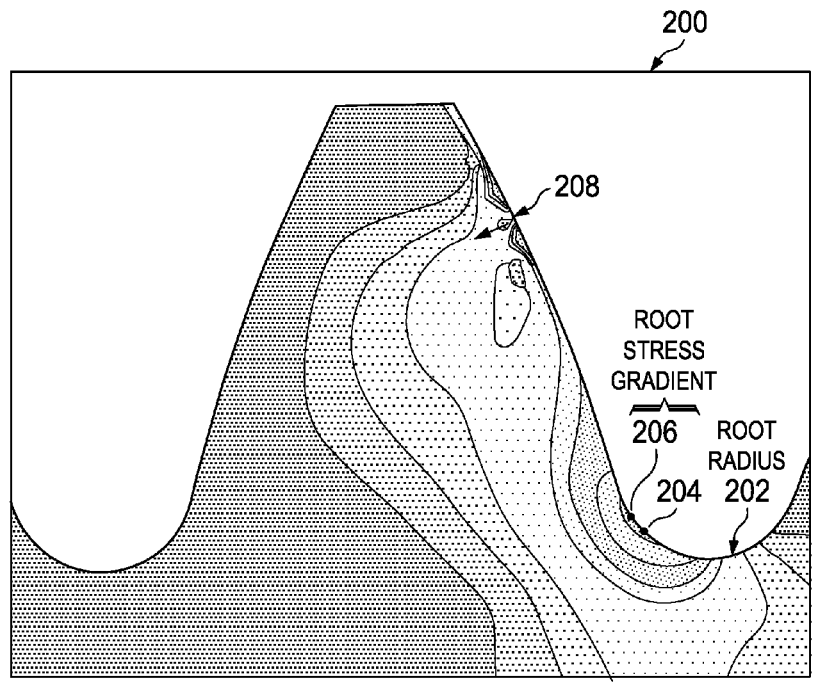
FIG. 2 is a partial view of a workpiece according to an embodiment of the disclosure.
Figure 3:
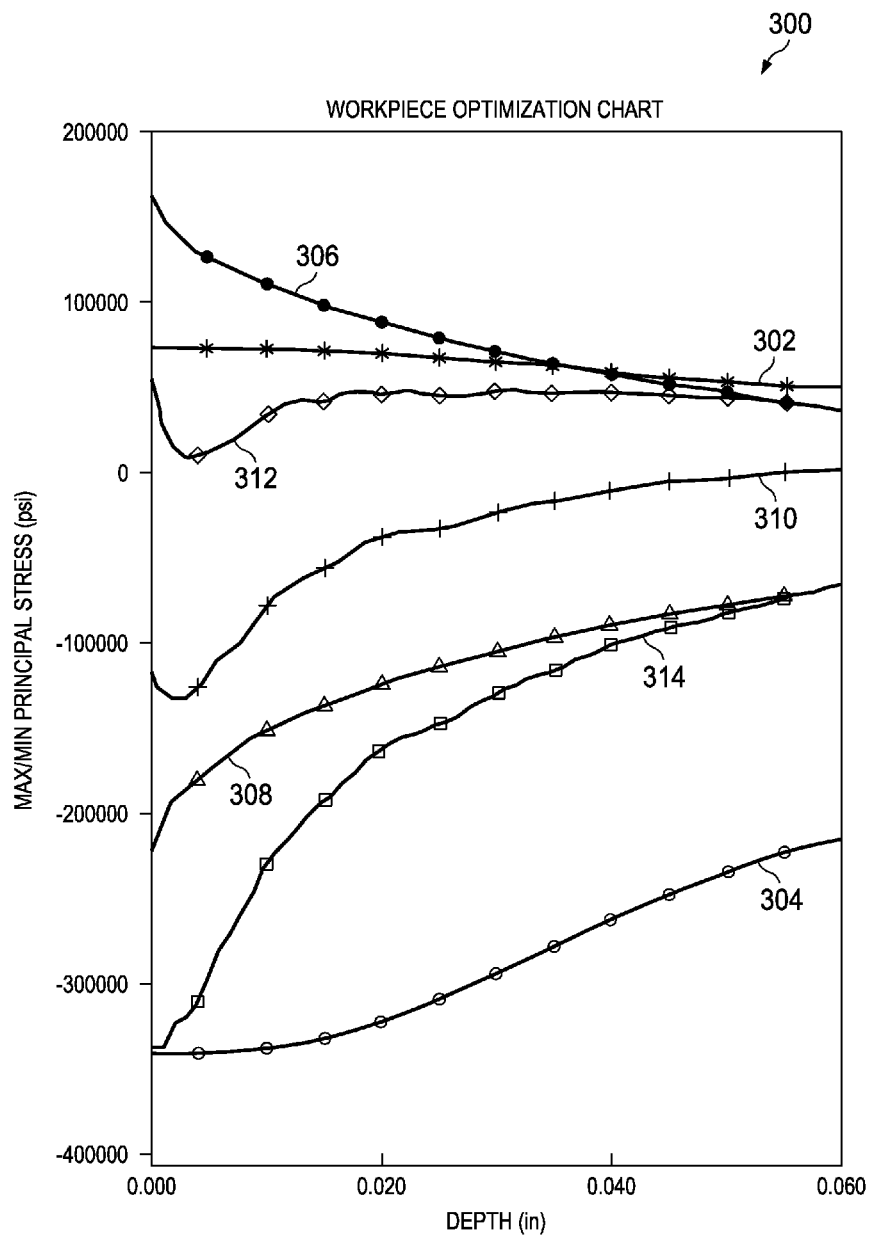
FIG. 3 is a workpiece optimization chart according to an embodiment of the disclosure.

Referring now to FIGS. 1-3, a method 100 of improving a workpiece, a gear 200 (a subject workpiece of the method 100), and a workpiece optimization chart 300 (showing the findings of various steps of the method 100) are shown, respectively. Most generally, the method 100 may be implemented to improve a workpiece, such as the gear 200 of FIG. 2, to improve the service life or strength of the gear 200 in accordance with the curves of FIG. 3 as described below.

The method 100 may begin at block 102 by determining workpiece tensile limits. Most generally, the term tensile may refer to workpiece strength limits as a load is generally applied to the workpiece in a first direction. In some embodiments, the workpiece tensile limits may be determined as a function of the material composition of the workpiece, the structure and/or shape of the workpiece, a working temperature of an environment in which the workpiece is anticipated to be utilized, a working temperature of the workpiece, and any already applied material treatment processes applied to the workpiece. In some cases, the workpiece tensile limits may be obtained from a manufacturer provided specification of the workpiece. In other cases, the tensile limits may be experimentally obtained through laboratory testing of a substantially identical workpiece. Regardless the method of obtaining the tensile limits of the workpiece, in some embodiments the workpiece tensile limits may be represented as a plot or curve of the maximum principal stress (as measured in pressure per square inch (psi) versus a dimension of the workpiece. In some cases, the tensile limit values may be plotted versus a depth below an outer surface of a tooth root 202 of the gear 200. As shown in FIG. 3, the workpiece tensile limit curve 302 is relatively flat with only a slight decrease in strength as measured deeper from the surface of the tooth root 202. Most generally, the depth may be considered to be measured in a direction parallel to a direction normal to the surface of a portion of the tooth root 202. However, because the tooth root 202 comprises a plurality of surface points from which a depth may be measured, it will be appreciated that the workpiece optimization chart 300 is directed mostly to a selected surface point 204 of the tooth root 202 and that workpiece optimization charts associated with other surface points of the tooth root 202 may yield different curves.

The method 100 may continue at block 104 by determining workpiece compressive limits. Most generally, the term compressive may refer to workpiece strength limits as a load is generally applied in a second direction that is generally opposed and/or opposite to the first direction. In some embodiments, the workpiece compressive limits may be determined as a function of the material composition of the workpiece, the structure and/or shape of the workpiece, a working temperature of an environment in which the workpiece is anticipated to be utilized, a working temperature of the workpiece, and any already applied material treatment processes applied to the workpiece. In some cases, the workpiece compressive limits may be obtained from a manufacturer provided specification of the workpiece. In other cases, the compressive limits may be experimentally obtained through laboratory testing of a substantially identical workpiece. Regardless of the method of obtaining the compressive limits of the workpiece, in some embodiments the workpiece compressive limits may be represented as a plot or curve of the maximum principal stress (as measured in psi) versus a dimension of the workpiece. In some cases, the compressive limit values may be plotted versus a depth below an outer surface of a tooth root 202 of the gear 200. As shown in FIG. 3, the workpiece compressive limit curve 304 may increase in strength as measured deeper from the surface of the root 202. It will be appreciated that while the workpiece tensile limits are denoted as positive pressure values, the workpiece compressive limit values are denoted as negative pressure values as a function of the opposite directional forces associated with the limits. The workpiece compressive limit curve 304 is measured relative to the selected surface point 204 of the tooth root 202 in a manner similar to that of the workpiece tensile limit curve 302. In some cases, the workpiece tensile limit curve 302 should not be exceeded by forces greater than the workpiece tensile limit curve 302 or the workpiece may deform. Similarly, the workpiece compressive limit curve 304 should not be exceeded by forces greater (or higher negative value as shown on workpiece optimization chart 300) or the workpiece may deform. Accordingly, the workpiece tensile limit curve 302 and the workpiece compressive limit curve 304 may bound or envelope operational values of forces or loads that the workpiece or gear 200 may withstand without deformation along the tooth root 202 as measured along a depth associated with the selected surface point 204.

The method 100 may continue at block 106 by determining a tensile load stress profile of the workpiece. More specifically, a known or anticipated load or combination of loads may be experimentally applied to the workpiece and/or applied to the workpiece through modeling via finite element analysis (whether computerized or otherwise) to determine a tensile load stress profile for the workpiece under the tensile load conditions. In some embodiments, the workpiece tensile load stress profile may be determined as a function of the material composition of the workpiece, the structure and/or shape of the workpiece, a working temperature of an environment in which the workpiece is anticipated to be utilized, a working temperature of the workpiece, and any already applied material treatment processes applied to the workpiece. In some cases, the workpiece tensile load stress profile may be obtained from a manufacturer provided specification of the workpiece. In other cases, the workpiece tensile load stress profile may be experimentally obtained through laboratory testing of a substantially identical workpiece. Regardless of the method of obtaining the workpiece tensile load stress profile of the workpiece, in some embodiments the workpiece tensile load stress profile may be represented as a plot or curve of the maximum principal stress (as measured in psi) versus a dimension of the workpiece. In some cases, the workpiece tensile load stress profile may be plotted versus a depth below the outer surface of the tooth root 202 of the gear 200. As shown in FIG. 3, the workpiece tensile load stress curve 306 may exceed the workpiece tensile limit curve 302 near the surface and decrease in strength as measured deeper from the surface of the tooth root 202. The workpiece tensile load stress curve 306 is measured relative to the selected surface point 204 of the tooth root 202 in a manner similar to that of the workpiece tensile limit curve 302. Because portions of the workpiece tensile load stress curve 306 are greater than the respective (based on depth) workpiece tensile limit curve 302 values, the workpiece optimization chart 300 may indicate that the workpiece may fail to handle the applied tensile load conditions without deformation. Accordingly, there may be an opportunity to improve the workpiece through the use of a variety of treatment processes to allow the workpiece to withstand the application of the tensile load conditions after the application of the treatment processes. The treatment process may comprise shot peening, carburizing, cavitation peening, laser peening, heat treatments, low plasticity burnishing, quenching, and/or any other suitable method of altering strength of the workpiece or gear 200, particularly at the surface of the workpiece or gear 200.

The method 100 may continue at block 108 by determining a compressive load stress profile of the workpiece. More specifically, a known or anticipated load or combination of loads may be experimentally applied to the workpiece and/or applied to the workpiece through modeling via finite element analysis (whether computerized or otherwise) to determine a compressive load stress profile for the workpiece under the compressive load conditions. In some embodiments, the workpiece compressive load stress profile may be determined as a function of the material composition of the workpiece, the structure and/or shape of the workpiece, a working temperature of an environment in which the workpiece is anticipated to be utilized, a working temperature of the workpiece, and any already applied material treatment processes applied to the workpiece. In some cases, the workpiece compressive load stress profile may be obtained from a manufacturer provided specification of the workpiece. In other cases, the workpiece compressive load stress profile may be experimentally obtained through laboratory testing of a substantially identical workpiece. Regardless of the method of obtaining the workpiece compressive load stress profile of the workpiece, in some embodiments the workpiece compressive load stress profile may be represented as a plot or curve of the maximum principal stress (as measured in psi) versus a dimension of the workpiece. In some cases, the workpiece compressive load stress profile may be plotted versus a depth below the outer surface of the tooth root 202 of the gear 200. As shown in FIG. 3, the workpiece compressive load stress curve 308 may not exceed the workpiece compressive limit curve 304. The workpiece compressive load stress curve 308 is measured relative to the selected surface point 204 of the tooth root 202 in a manner similar to that of the workpiece tensile limit curve 302. Because the workpiece compressive load stress curve 306 does not exceed (with greater negative values) the workpiece compressive limit curve 304 values, the workpiece optimization chart 300 may be referred to as indicating that the workpiece may handle the applied compressive load conditions without deformation.

The method 100 may continue at block 110 by determining a residual stress profile or residual stress curve 310 that when added to the workpiece tensile load stress curve 306, yields a resultant tensile stress curve 312 that does not exceed the workpiece tensile limit curve 302. In some embodiments, a residual stress curve 310 may be selected to produce a resultant tensile stress curve 312 that comprises a safe strength margin or offset between the resultant tensile stress curve 312 and the workpiece tensile load stress curve 306. In such cases, when the workpiece or gear 200 is provided with a residual stress curve 310 that suitably enables accommodation of the tensile load conditions described above, the workpiece will not deform in response to the application of the tensile load condition. However, the residual stress curve 310 must also be selected so that when a compressive load condition (such is sometimes the case in a gear 200 experiencing cyclical loading and/or directional changes in loading), a resultant compressive stress curve 314, defined as the summation of the residual stress curve 310 and the workpiece compressive load stress curve 308, does not exceed the workpiece compressive limit curve 304. If the compressive stress curve 314 exceeds the workpiece compressive limit curve 304, the workpiece may deform, or in the least, internally reconfigure to alter any previously provided residual stress designed to accommodate and/or offset the tensile load conditions.

The method 100 may progress to block 112 where the determined residual stress curve 310 is imparted to or provided to the workpiece or gear 200. In some embodiments, the residual stress curve 310 may be provided to the workpiece or gear 200 through any of the above-described workpiece treatment methods. However, in some embodiments, cavitation peening, laser peening, and/or low plasticity burnishing may be utilized where greater control or an ability to apply such treatments to only a relatively small selected portion of a workpiece or gear 200 is desired.

Referring now to FIG. 2, in some cases, the method 100 may be repeated in whole and/or in part for a single workpiece or gear 200 to be imparted with a plurality of different residual stress profiles. Not only can residual stress profiles be provided to the selected surface point 204 of tooth root 202, but other residual stress profiles may be applied at a second surface point 206 of tooth root 202 or at one or more mesh points 208 of gear 200. In other words, while the method 100 may generate a workpiece optimization chart 300 specific to a selected surface point, the method 100 may be generalized and applied at any surface point of a workpiece or gear 200. In some cases, the method 100 may first be applied to the gear 200 so that a workpiece tensile load stress curve 306 may be associated with a contact stress associated with the mesh point 208 of the gear 200 and the method 100 may secondly be applied to the gear 200 so that the workpiece tensile load stress curve 306 may be associated with a bending stress associated with the tooth root 202 of the gear 200. Accordingly, a gear 200 may be provided at least two different residual stress profiles tailored to the loading conditions of different features of the gear 200.

Still further, while method 100 is described as generating residual stress profiles as a function of depth of a workpiece, in alternative embodiments, the method 100 may be generalized and configured to provide residual stress profiles as a function of a variation in surface location along a predetermined translational path of the workpiece, such as a path along an external surface of the workpiece. For example, a predetermined external surface path of the workpiece may be defined and the residual stress profile may be provided as a function of the predetermined external surface path with the depth along the predetermined external surface path being a constant. Alternatively, in some embodiments, a two or three dimensional matrix, a spreadsheet, a computer model, and/or any other suitable manner of accommodating complex multidimensional data sets may be utilized so that a residual stress profile is not restricted to being applied to a particular selected location of a workpiece or gear 200. Rather, the residual stress profile may represent a complete or partial solution for a three dimensional space of the workpiece or gear 200. Accordingly, by generalizing the method 100, a particular workpiece may be evaluated for use in a predetermined set of loading conditions and thereafter may be treated so that, as a function of determining a residual stress solution for the workpiece (potentially as a whole) and providing the workpiece with the residual stress profile, the workpiece is optimized for exposure to the predetermined set of loading conditions and the life of the workpiece may be lengthened.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Unless otherwise stated, the term "about" shall mean plus or minus 10 percent of the subsequent value. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. A method of modifying a workpiece, comprising:
providing a workpiece;
determining a tensile load stress profile associated with a tensile load condition, the tensile load stress profile comprising a tensile load stress beyond a tensile stress limit of the workpiece;
determining a compressive load stress profile associated with a compressive load condition, the compressive load stress profile comprising a compressive load stress within a compressive stress limit of the workpiece;
determining a residual stress profile, the residual stress profile comprising a residual stress within the tensile stress limit of the workpiece, wherein a sum of the tensile stress and the residual stress is within the tensile stress limit and a sum of the compressive stress and the residual stress is within the compressive stress limit of the workpiece; and
providing the workpiece with the residual stress profile.

2. The method of claim 1, wherein the sum of the compressive stress and the residual stress is more positive than a compressive stress limit of the workpiece.

3. The method of claim 1, wherein the load condition is a cyclic load condition.

4. The method of claim 1, wherein the workpiece is a gear.

5. The method of claim 1, wherein the providing the workpiece with the residual stress profile comprises cavitation peening.

6. The method of claim 1, wherein the providing the workpiece with the residual stress profile comprises laser peening.

7. The method of claim 1, wherein the determining the compressive load stress profile or determining the tensile load stress profile comprises a finite element analysis of the workpiece.

8. The method of claim 1, wherein at least one of the compressive load stress profile and the residual stress profile are determined as a function of a depth of the workpiece.

9. The method of claim 1, wherein at least one of the compressive load stress profile and the residual stress profile are determined as a function of an outer profile translation path of the workpiece.

10. An apparatus comprising:
a processor configured to:
determine a tensile limit curve of the workpiece as a function of a dimension of the workpiece;
determine a compressive limit curve of the workpiece as a function of the dimension of the workpiece;
determine a tensile load stress profile associated with a tensile load condition, the tensile load stress profile comprising a tensile load stress curve as a function of the dimension of the workpiece;
determine a compressive load stress profile associated with a compressive load condition, the compressive load stress profile comprising a compressive load stress curve as a function of the dimension of the workpiece; and
determine a residual stress profile, the residual stress profile comprising a residual stress curve as a function of the dimension of the workpiece;
wherein a summation of the residual stress curve and the tensile load stress curve is less than the tensile limit curve of the workpiece along the dimension; and
wherein a summation of the residual stress curve and the compressive load stress curve is greater than the compressive limit curve along the dimension.

11. The apparatus of claim 10, wherein a direction of the first load condition is different than a direction of the second load condition.

12. The apparatus of claim 10, wherein the dimension is a depth of the workpiece.

13. The apparatus of claim 10, wherein the dimension is a translational path along an outer surface of the workpiece.

14. The apparatus of claim 10, wherein the workpiece is a gear.

15. The apparatus of claim 10, further configured to provide the residual stress profile to the workpiece.

16. An apparatus comprising:
a processor; and
a memory coupled to the processor, wherein the memory comprises instructions that cause the processor to:
determine a first contact stress associated with a mesh point of a tooth of a gear;
determine a first bending stress associated with a root of the tooth;
determine a first residual stress to the gear as a function of the first contact stress; and
provide a second residual stress as a function of the first bending stress.

17. The apparatus of claim 16, wherein a sum of the first contact stress and the first residual stress is less than a first stress limit of the tooth and wherein a sum of the first bending stress and the second residual stress is less than a second stress limit of the tooth.

18. The apparatus of claim 16, wherein a sum of the first contact stress limit and the first residual stress is greater than a first compressive yield limit of the tooth and wherein a sum of the first bending stress and the second residual stress is greater than a second compressive yield limit of the tooth.

19. The apparatus of claim 16, wherein at least one of the providing the first residual stress and providing the second residual stress comprises at least one of laser peening, cavitation peening, and low plasticity burnishing.

20. The apparatus of claim 16, wherein the first contact stress and the first residual stress are associated with a first depth associated with the mesh point and wherein the second contact stress and the second residual stress are associated with a first depth associated with the root.

* * * * *